United States Patent
Kim et al.

(10) Patent No.: US 8,354,842 B2
(45) Date of Patent: Jan. 15, 2013

(54) SEGMENTED MAGNETOSTRICTIVE PATCH ARRAY TRANSDUCER, APPARATUS FOR DIAGNOSING STRUCTURAL FAULT BY USING THE SAME, AND METHOD OF OPERATING THE SAME

(75) Inventors: Hoe Woong Kim, Seoul (KR); Young Eui Kwon, Seoul (KR); Yoon Young Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 609 days.

(21) Appl. No.: 12/640,602

(22) Filed: Dec. 17, 2009

(65) Prior Publication Data
US 2010/0259252 A1    Oct. 14, 2010

(30) Foreign Application Priority Data
Apr. 8, 2009 (KR) .................. 10-2009-0030498

(51) Int. Cl.
*G01N 27/82* (2006.01)
(52) U.S. Cl. ........ 324/240; 324/209; 324/219; 324/220; 324/221; 324/216; 324/228; 324/239; 324/232; 324/238; 324/225; 73/622; 73/628; 73/643
(58) Field of Classification Search .............. 324/209, 324/219–221, 216, 228, 239, 240, 232, 266, 324/225, 238; 73/637, 584, 596, 618, 620, 73/622, 623, 643, 570, 866.5, 865.8, 865.9
See application file for complete search history.

(56) References Cited

U.S. PATENT DOCUMENTS
710,254 A * 9/1902 Cooper .................. 301/135
(Continued)

FOREIGN PATENT DOCUMENTS
KR           100677920 B1        1/2007

OTHER PUBLICATIONS

Seung Hyun Cho et al., "High-frequency torsional modal testing of a long cylinder by magnetostriction", Applied Physics Letters, 91 (2007).*
Chan II Park et al., "Efficient Generation and Measurement of Guided Torsional Waves Using Magnetostrictive Nickel Patches", 2004 IEEE Ultrasonics Symposium, pp. 1290-1293 (2004).*
Hoe Woong Kim et al., "Shear-Horizontal Wave-Based Pipe Damage Inspection by Arrays of Segmented Magnetostrictive Patches", IEEE Transactions on Ultrasonics, Ferroelectrics and Frequency Control, vol. 55, No. 22, pp. 2689-2698 (2011).*

(Continued)

*Primary Examiner* — Reena Aurora
*Assistant Examiner* — Lamarr Brown
(74) *Attorney, Agent, or Firm* — Kile Park Goekjian Reed & McManus PLLC

(57) ABSTRACT

A segmented magnetostrictive patch array transducer capable of generating a high frequency shear wave in a structure such as a rod or a pipe, a structural fault diagnosing apparatus including the segmented magnetostrictive patch array transducer, and a method of operating the segmented magnetostrictive patch array transducer are shown. The segmented magnetostrictive patch array transducer includes a plurality of magnetostrictive patches attached along a circumference of a rod member; a plurality of insulators that are disposed on the magnetostrictive patches; a plurality of meander coils, each of the meander coils comprising a plurality of coil lines extending along the circumference direction of the rod member on each of the insulators, wherein a current flows through adjacent coil lines in opposite directions to one another; and a plurality of magnets that respectively form a magnetic field along the circumferential direction of the rod member on the magnetostrictive patches.

10 Claims, 13 Drawing Sheets

U.S. PATENT DOCUMENTS

| | | | | |
|---|---|---|---|---|
| 4,593,567 | A * | 6/1986 | Isselstein et al. | 73/643 |
| 6,250,163 | B1 * | 6/2001 | MacLauchlan et al. | 73/643 |
| 6,868,730 | B2 * | 3/2005 | Kim et al. | 73/643 |
| 6,920,792 | B2 * | 7/2005 | Flora et al. | 73/622 |
| 6,924,642 | B1 * | 8/2005 | Cho et al. | 324/240 |
| 7,098,655 | B2 * | 8/2006 | Yamada et al. | 324/235 |
| 7,165,453 | B2 * | 1/2007 | Flora et al. | 73/643 |
| 7,215,118 | B2 * | 5/2007 | Park et al. | 324/238 |
| 7,295,001 | B2 * | 11/2007 | Kim et al. | 324/209 |
| 7,406,873 | B2 * | 8/2008 | Paige et al. | 73/643 |
| 7,614,313 | B2 * | 11/2009 | Kim et al. | 73/862.333 |
| 7,621,189 | B2 * | 11/2009 | Kim et al. | 73/862.335 |
| 7,742,616 | B2 * | 6/2010 | Kim et al. | 381/396 |
| 2003/0205088 | A1 * | 11/2003 | Passarelli, Jr. | 73/643 |
| 2005/0179430 | A1 * | 8/2005 | Park et al. | 324/240 |
| 2006/0145692 | A1 * | 7/2006 | Kim et al. | 324/209 |
| 2006/0158181 | A1 * | 7/2006 | Shoji | 324/240 |
| 2006/0210100 | A1 * | 9/2006 | Kim et al. | 381/171 |
| 2007/0090904 | A1 * | 4/2007 | Kim et al. | 335/205 |
| 2009/0115411 | A1 * | 5/2009 | Sun et al. | 324/242 |
| 2010/0321009 | A1 * | 12/2010 | Lee et al. | 324/209 |

OTHER PUBLICATIONS

Seung Hyun Cho et al., "Megahertz-Range Guided Pure Torsional Wave Transduction and Experuments Using a Magnetostrictive Transducer", IEEE Transactions on Ultrasonics, Ferroelectrics and Frequency Control, col. 57, No. 5, pp. 1225-1229 (2010).*

Seung Hyun Cho et al., "Noncontact torsional wave transduction in a rotating shaft using oblique magnetostrictive strips", Journal of Applied Physics, 100 (2006).*

Cho, Seun Hyun et al., "Generation and Detection of Torsional Waves in a Rotating Shaft Using a Magnetorestrictive Patch Array", Transactions of the Korean Society of Mechanical Engineers, vol. 30 No. 3, pp. 342-348, 2006.

* cited by examiner 500 kHz 90cm angular profile

SEGMENTED MAGNETOSTRICTIVE PATCH ARRAY TRANSDUCER, APPARATUS FOR DIAGNOSING STRUCTURAL FAULT BY USING THE SAME, AND METHOD OF OPERATING THE SAME

CROSS-REFERENCE TO RELATED PATENT APPLICATION

This application claims the benefit of Korean Patent Application No. 10-2009-0030498, filed on Apr. 8, 2009, in the Korean Intellectual Property Office, the disclosure of which is incorporated herein in its entirety by reference.

BACKGROUND OF THE INVENTION

1. Field of the Invention

The present invention relates to a magnetostrictive transducer, and a method and apparatus for non-destructive testing of structural defects, and more particularly, to a transducer that generates a shear wave partially on a circumference of a beam, or a pipe having a predetermined cross-section such as a circle and measures and analyses the shear wave which returns after being reflected by a defect, an apparatus for detecting a defect and the position (distance and angle) of the defect in a structure, and a method of operating the transducer.

The present invention was derived from a research project sponsored by the Korea Science and Engineering Foundation and Seoul National University R&DB Foundation.

[2009-0083279, Multi-Scale Paradigm for Creative Design of Multi-Physical Complex Structure System].

2. Description of the Related Art

Magnetostriction refers to mechanical deformation of ferromagnetic materials in a magnetic field. It is also referred as the Joule effect. An inverse effect thereof is referred as an inverse magnetostrictive effect or the Villari effect in which a magnetic state of a material changes when stress is applied thereto. Magnetostriction may be used to measure the deformation of an object without mechanically contacting the object, and is thus widely employed in various fields where contact type sensors cannot be used. In the case of magnetostriction, an elastic wave may be generated contactlessly, and furthermore, a larger elastic guided wave may be generated compared to the case when the conventional piezoelectric effect is used. Examples of inductive ultrasonic waves that may be generated in a waveguide such as a rod or a pipe are a longitudinal wave, a flexural wave, and a torsional wave. For example, in a first mode of the torsional wave, dispersion, which results in speed differences of the torsional wave due to frequency components, does not exist, and thus a structural defect may be effectively diagnosed. Also, a shear wave may be generated partially on the structure, and since a first mode of the shear wave also has non-dispersion characteristics, like the torsional wave, the shear wave may also be efficiently used in monitoring defects.

FIGS. 1 through 3 illustrate a torsional vibration in a rod member when magnetostriction is used and the principle of measuring the torsional vibration.

Referring to FIG. 1, when a first magnetic field $B_S$ and a second magnetic field $B_D$ are applied perpendicularly to each other near a ferromagnetic strip 1, the strip 1 may be deformed in a shearing direction as illustrated in FIG. 2. That is, the first magnetic field $B_S$ is a static magnetic field, which is maintained constant, and the second magnetic field $B_D$ is a dynamic magnetic field. The strip 1 is deformed according to the variation of the second magnetic field $B_D$ as illustrated in FIG. 2.

Referring to FIG. 3, the above principle is explained in relation to a rod member. The strip 1 is attached along the circumference of a rod member 2. Then, a static magnetic field $B_S$ is applied around the strip 1, and a variable dynamic magnetic field $B_D$ is applied in a length direction of the rod member 2 that substantially perpendicularly crosses the static magnetic field $B_S$. Thus, a torsional vibration may be generated in the rod member 2 according to the deformation of the strip 1.

FIGS. 4 and 5 schematically illustrate the configurations of conventional magnetostrictive transducers for generating a torsional wave.

Referring to FIG. 4, the conventional magnetostrictive transducer that generates a torsional wave includes a thin ferromagnetic strip 1 which is wound around a rod member 2 in the circumferential direction of the rod member 2, an insulator 4 that is installed on the circumference of the strip 1, and a solenoid coil 3 that is wound around the insulator 4. In order to generate a torsional wave in the magnetostrictive transducer having the above-described configuration, the ferromagnetic strip 1 need to be rubbed using a magnet in order to pre-magnetize the ferromagnetic strip 1.

However, the ferromagnetic strip 1 may not be uniformly pre-magnetized, and thus, measurement repetitiveness may not be ensured.

To avoid pre-magnetizing the ferromagnetic strip 1, a method of forming a magnetic field in a ferromagnetic strip 1' in a desired direction by further disposing a magnet 6 in the magnetostrictive transducer of FIG. 4 as illustrated in FIG. 5 has been suggested.

However, in this case, although a structure may be monitored by generating a torsional wave, only a distance between a measuring unit and a position of a structural crack may be measured, and additional information such as an angular position along a circumferential direction in a waveguide may not be obtained.

SUMMARY OF THE INVENTION

The present invention provides a transducer that generates a high frequency shear wave in a structure such as a rod or a pipe, and an apparatus for diagnosing a structural fault whereby a structural defect is detected, and a distance from a measuring point to the structural defect and a circumferential angle of the defect in a circumferential direction are precisely measured by using a shear wave generated by the transducer.

The present invention also provides a method of operating a transducer in order to control a propagating direction of a shear wave generated by the transducer.

According to an aspect of the present invention, there is provided a segmented magnetostrictive patch array transducer comprising: a plurality of magnetostrictive patches attached along a circumference of a rod member; a plurality of insulators disposed on the magnetostrictive patches; a plurality of meander coils, each of the meander coils comprising a plurality of coil lines extending along the circumferential direction of the rod member on each of the insulators, wherein a current flows through adjacent coil lines in opposite directions to one another; and a magnetic field forming unit having a plurality of magnets that respectively form a magnetic field along the circumferential direction of the rod member on the magnetostrictive patches, wherein when a current is applied to at least one meander coil, the magnetostrictive patch located near the corresponding coil line of the meander coil is deformed due to magnetostriction so that a shear wave is generated along the rod member, or when the magnetostrictive patches are deformed due to a wave transmitted along the rod member, an electromotive force is generated in the meander coil due to an inverse magnetostrictive effect.

A distance between the coil lines is half of a wavelength of the generated shear wave.

The magnets are respectively disposed between the magnetostrictive patches.

According to another aspect of the present invention, there is provided a structural fault diagnosing apparatus comprising: a magnetostrictive patch that is attached to a surface of a rod member and is formed of a ferromagnetic material; an insulator that is disposed on the magnetostrictive patch; a meander coil that comprises a plurality of coil lines extending along a circumferential direction of the rod member on the insulator, wherein a current flows through adjacent coil lines in opposite directions to one another; at least one magnet that forms a magnetic field along the circumferential direction of the rod member on the magnetostrictive patch; and an array sensor comprising a plurality of sensor units, wherein when a current flows through the meander coil, the magnetostrictive patch deforms due to a magnetostrictive effect so that a shear wave is generated along the rod member, and the plurality of sensor units that are disposed at predetermined intervals along the circumferential direction of the rod member sense the shear wave.

The array sensor comprises: a plurality of magnetostrictive patches attached to a circumference of the rod member; a plurality of insulators that are respectively disposed on the plurality of the magnetostrictive patches; a plurality of meander coils, each of the meander coils comprising a plurality of coil lines extending along a circumferential direction of the rod member on the insulators, wherein a current flows through adjacent coil lines in opposite directions to one another; and a magnetic field forming unit that forms a magnetic field along a circumferential direction of the rod member on the magnetostrictive patches, wherein an electromotive force is generated in the meander coil due to an inverse magnetostrictive effect as the magnetostrictive patches are deformed due to a shear wave, and an amplitude of the shear wave is measured by measuring the electromotive force.

A distance between the coil lines is half of a wavelength of the generated shear wave.

According to another aspect of the present invention, there is provided a method of operating a segmented magnetostrictive patch array transducer, wherein the segmented magnetostrictive patch array transducer comprises: a plurality of magnetostrictive patches attached along a circumference of a rod member; a plurality of insulators that are respectively disposed on the magnetostrictive patches; a plurality of meander coils, each of the meander coils comprising a plurality of coil lines extending along a circumferential direction of the rod member on the insulators, wherein a current flows through adjacent coil lines in opposite directions to one another; and a magnetic field forming unit that forms a magnetic field along the circumferential direction of the rod member on the magnetostrictive patches, wherein when a current is applied to at least one meander coil, a magnetostrictive patch located near the corresponding coil line of the meander coil is deformed due to magnetostriction so that a shear wave is generated along the rod member, or when the magnetostrictive patch is deformed due to a wave transmitted along the rod member, an electromotive force is generated in the meander coil due to an inverse magnetostrictive effect, the method comprising: controlling instants of times when a current is applied to each meander coil in order to control instants of times when shear waves are generated using a deformation of each of the magnetostrictive patches so as to control points where waves respectively generated from each of the magnetostrictive patches and transmitted along the rod member generate a constructive interference.

According to another aspect of the present invention, there is provided a segmented magnetostrictive patch array transducer comprising: a magnetostrictive patch attached along a circumference of a rod member; an insulator that is disposed on the magnetostrictive patch; a plurality of meander coils, each of the meander coils comprising a plurality of coil lines extending along a circumferential direction of the rod member on the insulator, wherein a current flows through adjacent coil lines in opposite directions to one another; and a magnetic field forming unit that forms a magnetic field along the circumferential direction of the rod member on the magnetostrictive patch, wherein an area on the magnetostrictive patch wound around the circumference of the rod member is divided into a plurality of portions along the circumference of the rod member, and the plurality of meander coils are arranged to respectively correspond to the divided portions of the area, wherein when a current is applied to at least one of the meander coils, the magnetostrictive patch located near the corresponding meander coil is deformed due to magnetostriction so that a shear wave is generated along the rod member, or when the magnetostrictive patch is deformed due to a wave transmitted along the rod member, an electromotive force is generated in the meander coil due to an inverse magnetostrictive effect.

According to another aspect of the present invention, there is provided a segmented magnetostrictive patch array transducer comprising: a magnetostrictive patch attached along a circumference of a rod member; an insulator that is disposed on the magnetostrictive patch to cover the magnetostrictive patch; a meander coil that comprises a plurality of coil lines extending along a circumferential direction of the rod member on the insulator, wherein a current flows through adjacent coil lines in opposite directions to one another; and a magnetic field forming unit that forms a magnetic field along a circumferential direction of the rod member on the magnetostrictive patch, wherein when a current is applied to the meander coil, the magnetostrictive patch located near the corresponding meander coil is deformed due to magnetostriction so that a shear wave is generated along the rod member, or when the magnetostrictive patch is deformed due to a wave transmitted along the rod member, an electromotive force is generated in the meander coil due to an inverse magnetostrictive effect.

The magnetic field forming unit comprises a plurality of electromagnets that are separated apart from one another along the circumference of the rod member.

According to the present invention, by generating a large shear wave, a defect in a structure such as rod or a pipe may be precisely detected, and a propagating direction of a generated shear wave may be controlled by controlling a plurality of transducers units. Also, not only a distance between a sensor and a defect but also a circumferential angle of the defect in a rod member may be measured.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
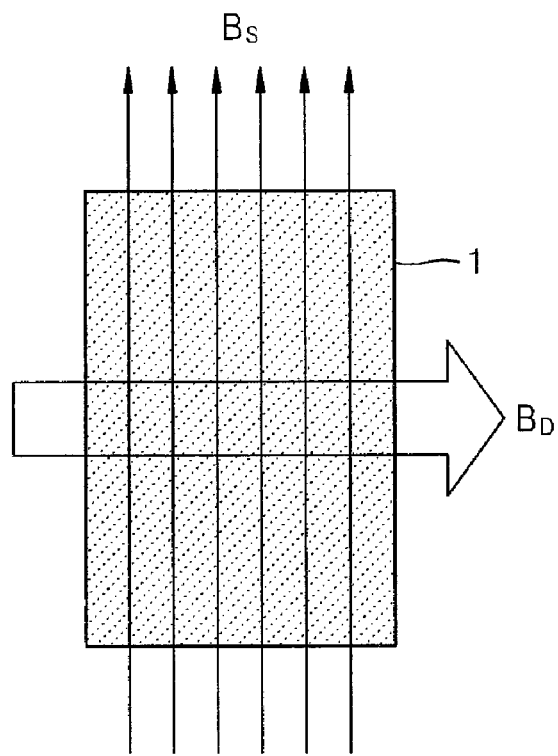
FIGS. 1 through 3 illustrate a torsional vibration in a rod member when magnetostriction is used and the principle of measuring the torsional vibration.
Figure 2:
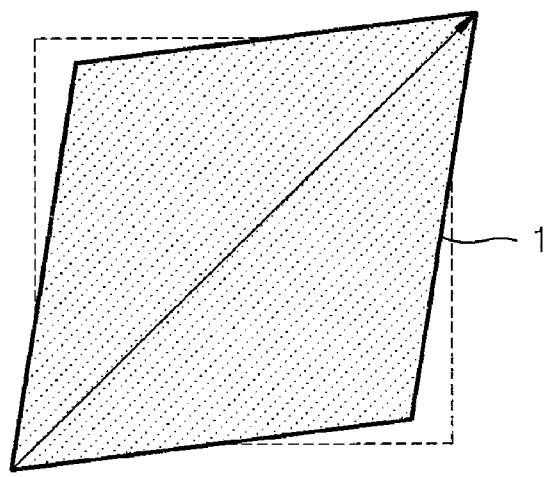
Figure 3:
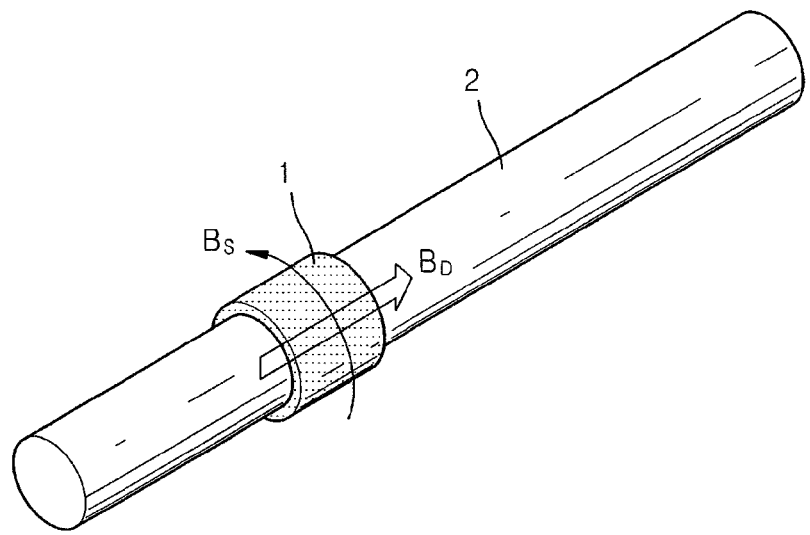
Figure 4:
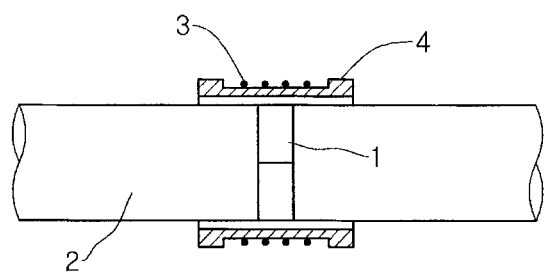
FIG. 4 illustrates an example of a conventional magnetostrictive transducer for generating a torsional wave.
Figure 5:
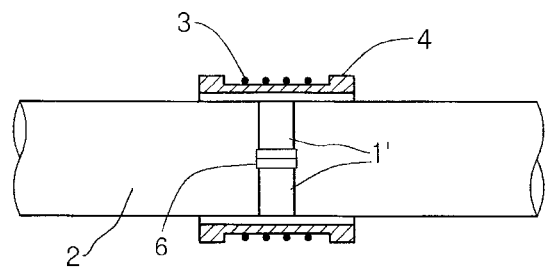
FIG. 5 illustrates another example of a conventional magnetostrictive transducer for generating a torsional wave.
Figure 6:
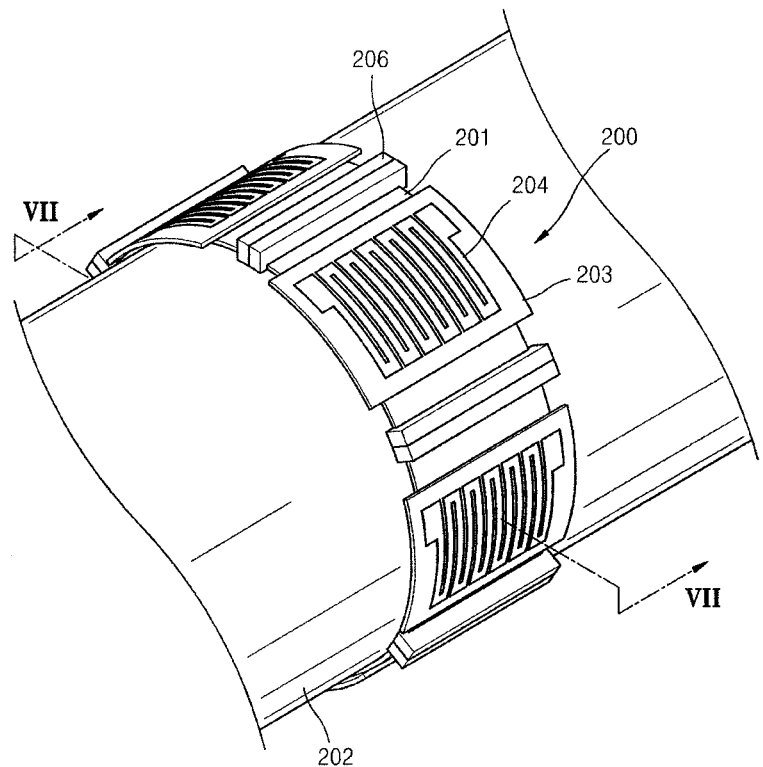
FIG. 6 is a perspective view illustrating a segmented magnetostrictive patch array transducer according to an embodiment of the present invention.
Figure 7:
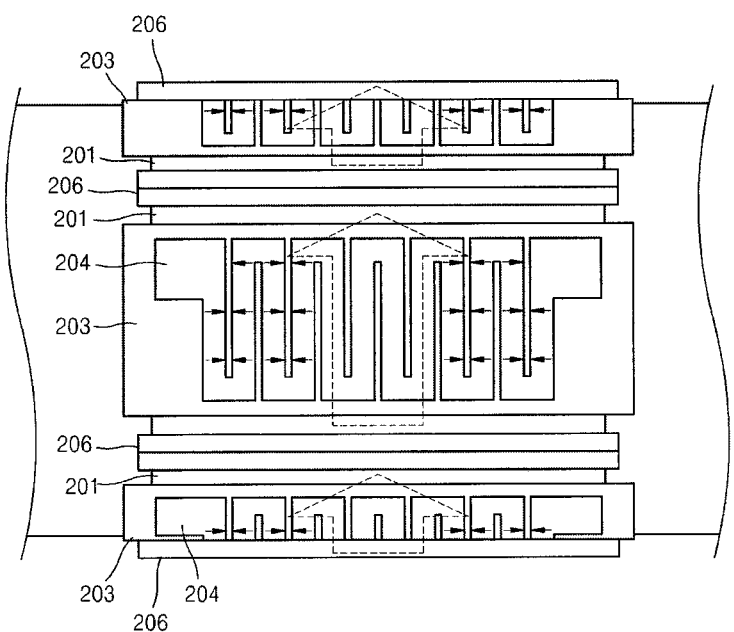
FIG. 7 is a side view of the segmented magnetostrictive patch array transducer illustrated in FIG. 6.
Figure 8:
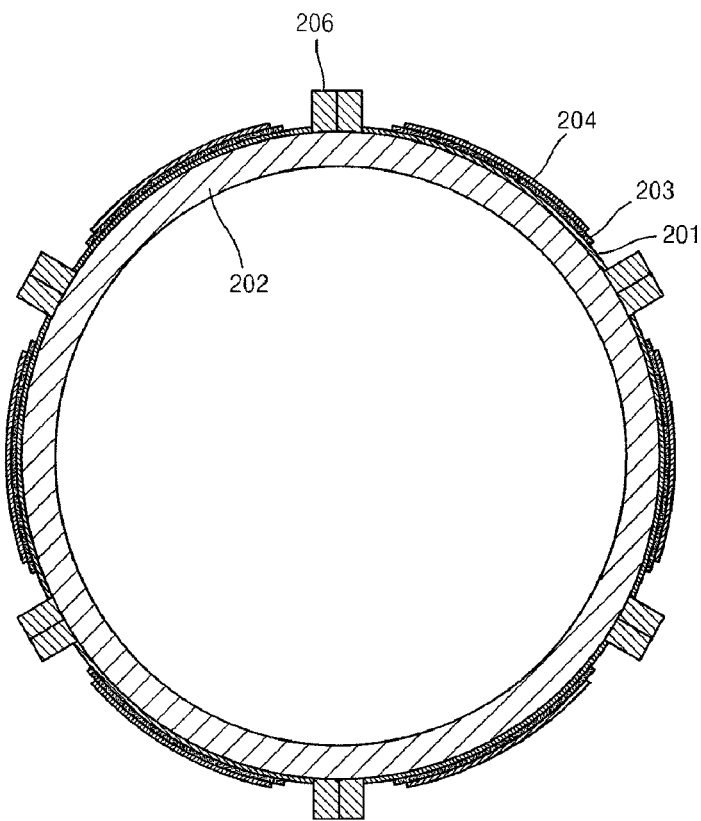
FIG. 8 is a cross-sectional view illustrating the segmented magnetostrictive patch array transducer of FIG. 6 along a line VIII-VIII.

FIG. 6 is a perspective view illustrating a segmented magnetostrictive patch array transducer 200 according to an embodiment of the present invention. FIG. 7 is a side view of the segmented magnetostrictive patch array transducer 200 illustrated in FIG. 6. FIG. 8 is a cross-sectional view illustrating the segmented magnetostrictive patch array transducer 200 of FIG. 6 along a line VIII-VIII.

Referring to FIGS. 6 through 8, the segmented magnetostrictive patch array transducer 200 includes a plurality of magnetostrictive patches 201, a plurality of insulators 203 respectively disposed on the magnetostrictive patches 201, a plurality of bias magnet 206, and a meander coil 204 disposed on each of the insulators 203.

The magnetostrictive patches 201 are attached along a circumference of a rod member 202 to be tested. The plurality of magnetostrictive patches 201 have the same shape and thickness and may preferably be formed of a ferromagnetic material such as iron (Fe), nickel (Ni), or cobalt (Co), or an alloy thereof, or a material having high magnetostriction.

The insulator 203 provides electrical insulation between the magnetostrictive patches 201 and the meander coil 204.

The meander coil 204 includes a plurality of coil lines, has an overall meandering shape, and is disposed on an upper surface of the insulator 203. Each of the coil lines extends along a circumferential direction of the rod member 202, and adjacent coil lines are connected to each other at respective first and second ends thereof. Accordingly, when a current flows through the meander coil 204, the directions of currents flowing through adjacent coil lines are opposite to each other.

Meanwhile, a distance between the coil lines with respect to center lines of the coil lines may preferably be adjusted to be half the wavelength of a shear wave generated by the segmented magnetostrictive patch array transducer 200 according to the current embodiment of the present invention. This is because shear waves generated by magnetic fields supplied by adjacent coil lines do not offset each other but generate a constructive interference, thereby being possible to generate a larger shear wave. This will be described more in detail below with reference to FIGS. 9 and 10.

The magnet 206 applies a static magnetic field to the magnetostrictive patch 201 along a circumferential direction of the rod member 202, and may be disposed between every two of the magnetostrictive patches 201 as illustrated in FIGS. 6 through 8. Alternatively, the magnet 206 may be disposed in any manner as long as a static magnetic field is applied to the magnetostrictive patch 201 along a circumferential direction of the rod member 202. For example, the magnet 206 may be disposed not to be adjacent to the rod member 202 but be fixed to an external supporting unit and disposed near the magnetostrictive patch 201 to form a magnetic field along the magnetostrictive patch 201.

Meanwhile, a yoke for facilitating formation of a magnetic field may be further disposed between the magnetostrictive patches 201 and the magnets 206.

Hereinafter, generation of a shear wave using a segmented magnetostrictive patch array transducer according to an embodiment of the present invention will be described in detail with reference to FIGS. 9 and 10. Hereinafter, the segmented magnetostrictive patch array transducer will be referred as the array transducer, and a portion of a magnetostrictive patch of the array transducer including one insulator, one meander coil (disposed on the magnetostrictive patch), and a magnet that forms a magnetic field along a circumferential direction of a rod member to the magnetostrictive patch will be referred as a transducer unit. In other words, in FIGS. 6 through 8, six transducer units are disposed on a circumference of a rod member to constitute one array transducer.

Meanwhile, hereinafter, an array sensor is a unit that has the same configuration as the array transducer but has a sensing function instead of a generation function. Likewise, a sensor unit is a unit that has the same configuration as the transducer unit but has a sensing function.

Figure 9:
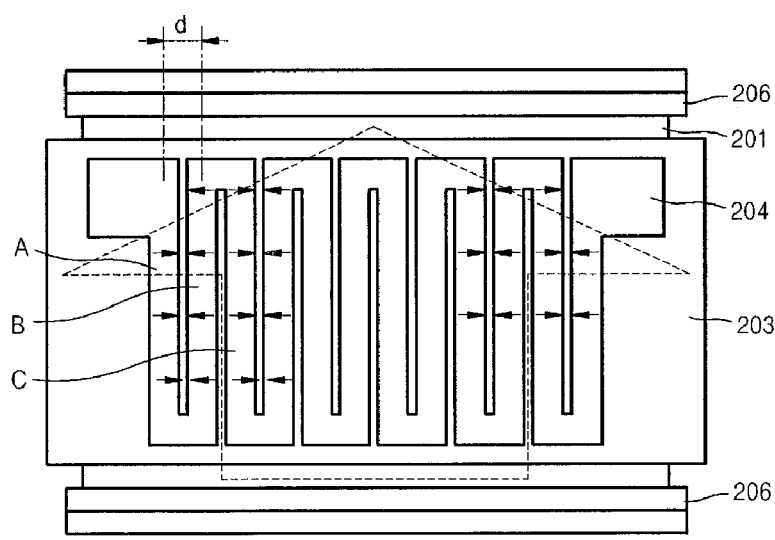
FIG. 9 is a schematic view illustrating a direction of a magnetic field in a segmented magnetostrictive patch array transducer according to an embodiment of the present invention.
Figure 10:
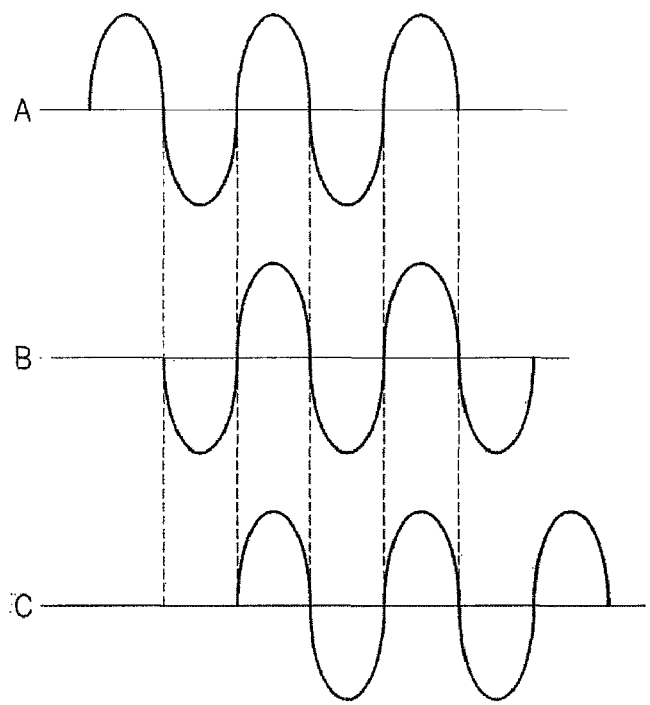
FIG. 10 is a schematic view illustrating shear waves respectively generated at corresponding positions of coil lines and superposed with one another.

FIG. 9 is a schematic view illustrating a direction of a magnetic field in a transducer unit according to an embodiment of the present invention. FIG. 10 is a schematic view illustrating shear waves generated at corresponding positions of each of coil lines and superposed with one another.

Referring to FIG. 9, a magnetic field is formed by a magnet 206 in a direction around a circumference of a rod member 202. When a current flows through a coil line extended along the circumference of the rod member 202, a magnetic field is formed in the magnetostrictive patch 201 disposed below the coil line in parallel to a length direction of the rod member 202. Due to the magnetic field formed by the magnet 206 and the magnetic field formed by the current flowing through the coil line, a shear wave is generated by magnetostriction occurring below the coil line of the magnetostrictive patch 201.

When a shear wave is generated below a coil line indicated by A, a shear wave is generated below a coil line B that is adjacent to the coil line A. The shear wave generated below the coil line B has a phase different by 180 degree from the phase of the shear wave generated below the coil line A. As described above, a distance d between centerlines of the coil lines A and B corresponds to half of the wavelength of the generated shear wave. Accordingly, since the positions where the shear waves are generated differ from each other by half of the wavelength of the shear waves and the shear waves generated in each of the coil lines have opposite phases, a constructive interference occurs consequently. Likewise, shear waves generated below a coil line C or other subsequent coil lines have the same phases, thereby generating a constructive interference. That is, the shear waves are amplified as many times as the number of coil lines, and thus a larger shear wave is generated in the rod member 202 and transmitted therein.

Figure 11:
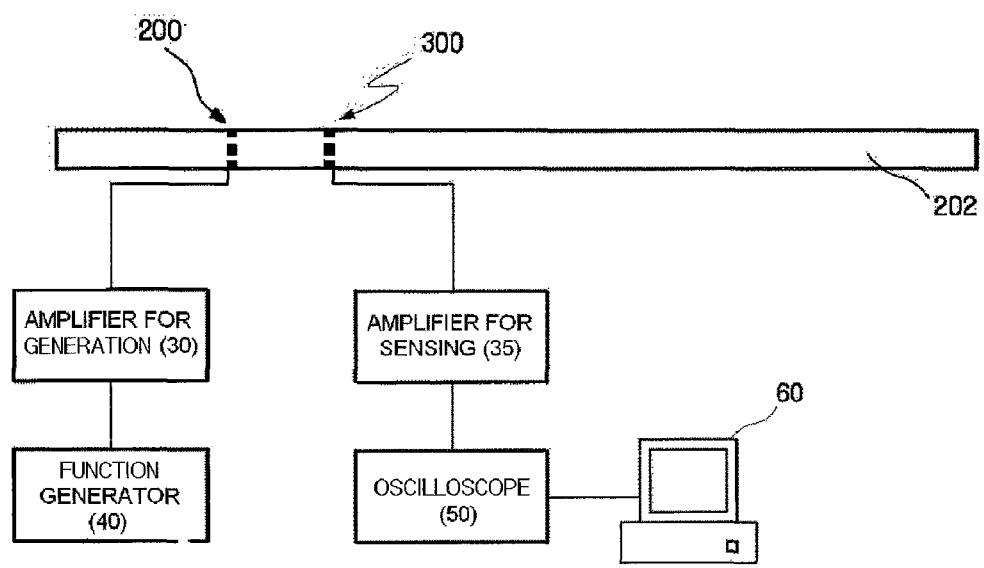
FIG. 11 is a schematic view illustrating a structural fault diagnosing apparatus including a segmented magnetostrictive patch array transducer according to an embodiment of the present invention.

FIG. 11 is a schematic view illustrating a structural fault diagnosing apparatus including an array transducer according to an embodiment of the present invention. Hereinafter, it will be considered that the array transducer performs an actuation function (substantially wave generation function).

Referring to FIG. 11, the structural fault diagnosing apparatus according to the current embodiment of the present invention includes an array transducer 200, an array sensor 300, a power amplifier 30, a function generator 40, a preamplifier 35, an oscilloscope 50, and a computer 60.

The array transducer 200 is the same as the array transducer 200 described with reference to FIGS. 6 through 10.

The array sensor 300 may have the same configuration as the array transducer 200 or may be omitted if a range of voltage of the amplifiers 30 and 35 is large, according to the configuration of peripheral apparatuses. When the array sensor 300 is omitted, the array transducer 200 may both generate a wave and measure the reflected wave.

The function generator 40 generates a wave in a form desired by the user. The generated wave is input to the power amplifier 30. The power amplifier 30 is connected to the array transducer 200, and amplifies a driving current for generating the wave and applies the same to the array transducer 200. A bias magnetic field along the circumferential direction by the magnet 206 and a variable magnetic field in an axial direction of the rod member 202 due to a current flowing through the meander coil 204 are applied to the magnetostrictive patch 201. Accordingly, the magnetostrictive patch 201 generates a torsional wave or a shear wave along the rod member 202 by magnetostriction.

The preamplifier 35 receives a voltage signal that is induced to the meander coil 204 of the array sensor 300 by a reflected wave of a torsional wave or a shear wave which returns after being reflected by two ends of the rod member 202 or cracks in the rod member 202, and amplifies the voltage signal.

The voltage signal that is received and amplified may be input also to the oscilloscope 50. The user may observe the amplified voltage signal and the waveform of the amplified voltage signal by using the oscilloscope 50. The computer 60 controls the power amplifier 30, the preamplifier 35, the function generator 40, and the oscilloscope 50 according to a command of a user, and stores a signal output by the oscilloscope 50 for further analysis.

In the structural fault diagnosing apparatus having the above configuration, one of transducer units of the array transducer 200 is selected to generate a shear wave, and the shear wave is measured by each of a plurality of sensor units of the array sensor, thereby sensing a position of a crack in the rod member 202. That is, a distance between the sensor units and the crack may be measured along a length direction of the rod member 202, and an angle at which the crack is located along the circumferential direction of the rod member 202 may be measured. The angle may be measured more accurately when more sensor units are used. For example, in an array sensor including six sensor units, an angle at which a defect is located may be measured in units of 60 degrees.

Also, a vibration that is sequentially applied to the plurality of transducer units disposed in the array transducer is measured by each of the sensor units, and by combining values measured several times using the sensor units, a position of a crack may be determined more accurately.

In the current embodiment, we only explained the actuation function (namely wave generation function) of the transducer included in the structural fault diagnosing apparatus according to the present invention. However, the transducer according to the present invention can both generate and sense a wave.

Figure 12:
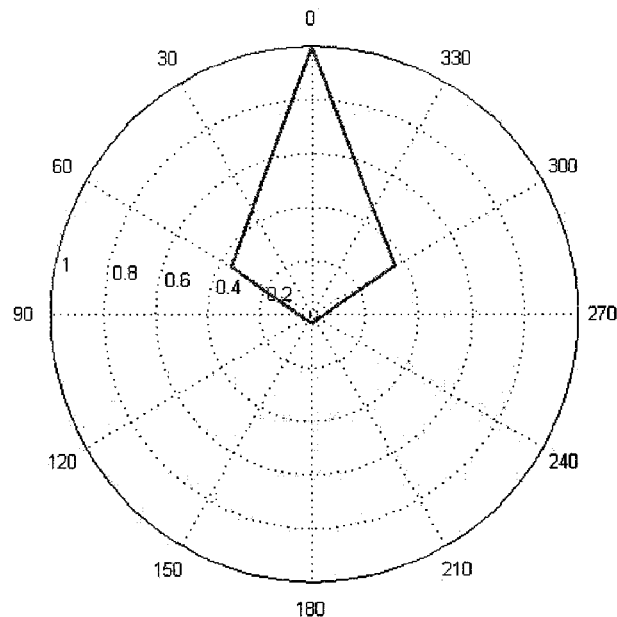
FIGS. 12 through 14 are schematic views of measured results obtained by generating a vibration in a defect-less pipe using a structural fault diagnosing apparatus as illustrated in FIG. 11 and measuring the vibration by using an array sensor.
Figure 13:
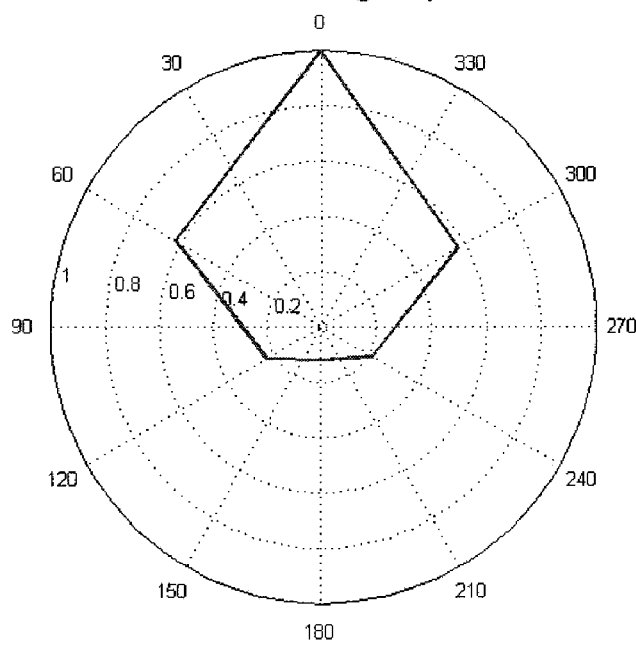
Figure 14:
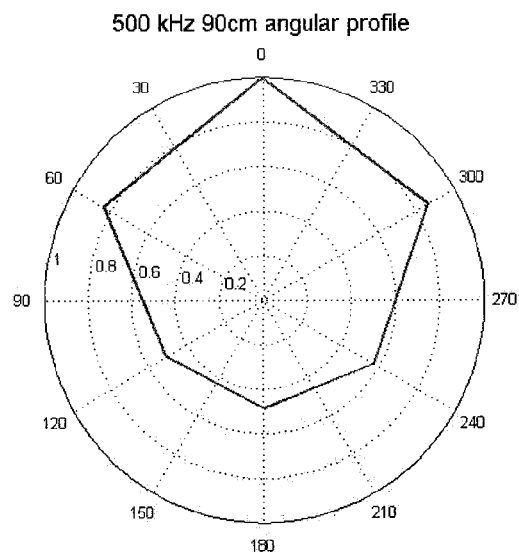

FIGS. 12 through 14 are schematic views illustrating measurement results obtained by applying a vibration to a defectless pipe using the structural fault diagnosing apparatus illustrated in FIG. 11.

The measurements were conducted under the following conditions. Six transducer units and six sensor units were respectively installed on a stainless seamless pipe having an outer diameter of 76.3 mm, a thickness of 2.1 mm, and a length of 2 m. A wave frequency was 500 kHz, and a size of the magnetostrictive patch 201 was 36×25×0.15 (Height× Width×Thickness) (mm). FIG. 12 shows a shear wave that is generated by the array transducer and measured by the sensor units when a distance between the array transducer and the array sensor was 30 cm. FIG. 13 shows a shear wave that is generated by the array transducer and measured by the sensor units when a distance between the array transducer and the array sensor was 60 cm. FIG. 14 shows a shear wave that is generated by the array transducer and measured by the sensor units when a distance between the array transducer and the array sensor was 90 cm.

Referring to FIGS. 12 through 14, a largest value was measured by the sensor unit disposed along the same circumferential direction as the generating transducer unit, and in this case, as the shear wave propagated in the length direction of the pipe, the shear wave was spread along the circumferential direction of the pipe. The same result was obtained by selecting one of transducer units of the array transducer and generating a vibration. The amplitude of the shear waves illustrated in FIGS. 12 through 14 varies between 0 and 1, showing the relative normalized amplitude.

Hereinafter, an experimental example for detecting a position of an actual defect by using a structural fault diagnosing apparatus according to an embodiment of the present invention will be described with reference to FIGS. 15 through 21.

Figure 15:
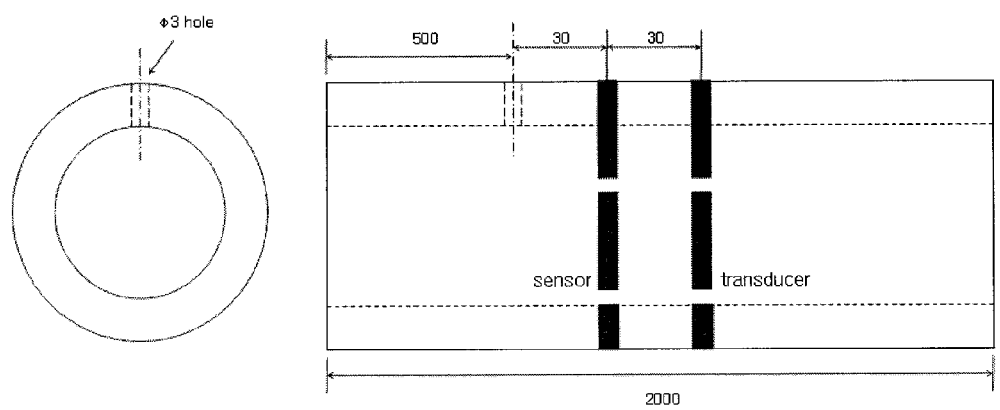
FIG. 15 is a schematic view illustrating a cross-section of a pipe used in an experiment for detecting the position of a defect, and the position and shape of the defect, and the positions of a transducer and a sensor, according to an embodiment of the present invention.
Figure 16:
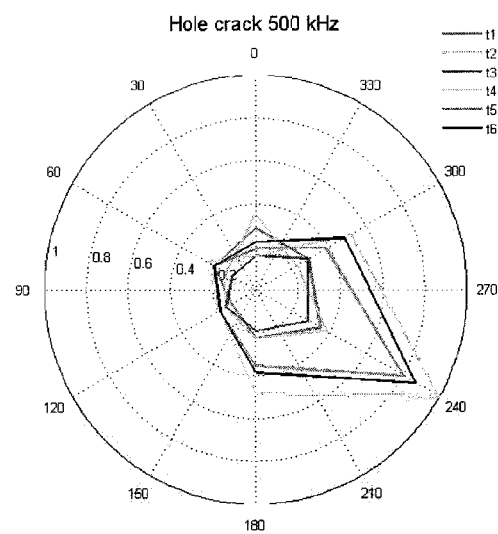
FIG. 16 is a graph showing relative amplitudes of reflected waves measured in sensor units in the experiment described with reference to FIG. 15.

FIG. 15 is a schematic view illustrating a cross-section of a pipe used in an experiment for detecting a defect, and the position and shape of the defect, and positions of transducer units and sensor units, according to an embodiment of the present invention. FIG. 16 is a graph showing relative amplitudes of reflected waves measured by sensor units in the experiment described with reference to FIG. 15. The transducer units and the sensor units are disposed at an angle of 60 degrees with respect to each other.

In the configuration illustrated in FIG. 15, a wave frequency was 500 kHz, and it was generated by the array transducer. As a result, as illustrated in FIG. 16, the largest measurement value was detected by a sensor unit corresponding to an angle of 240 degrees of a through hole having a diameter of 3 mm.

Figure 17:
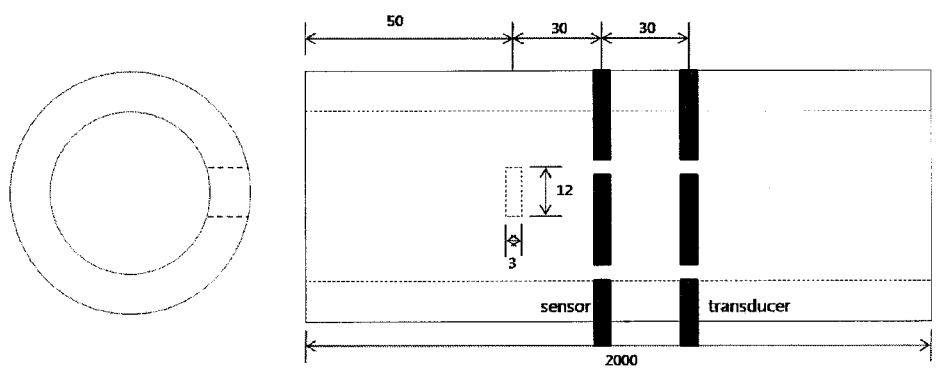
FIG. 17 is a schematic view illustrating a cross-section of a pipe used in another experiment for detecting the position of a defect, and the position and shape of the defect, and the positions of a transducer and a sensor, according to an embodiment of the present invention.
Figure 18:
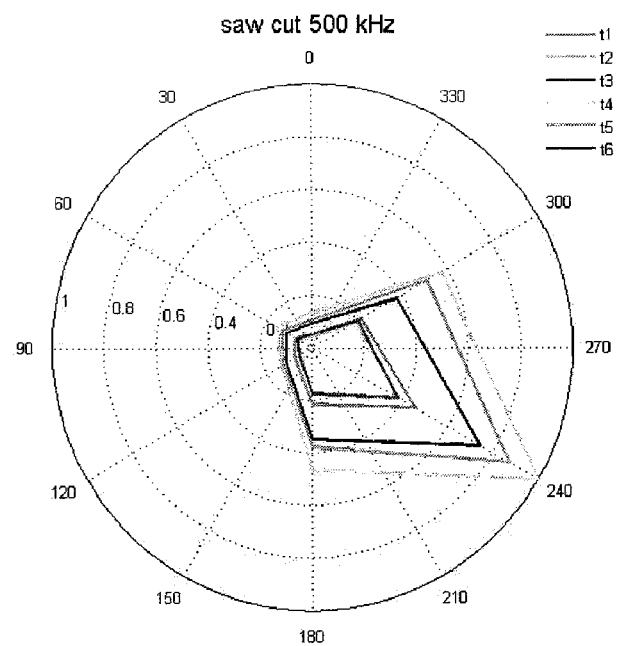
FIG. 18 is a graph showing relative amplitudes of reflected waves measured in sensor units in the experiment described with reference to FIG. 17.

FIG. 17 is a schematic view illustrating a cross-section of a pipe used in another experiment for detecting a defect, and the position and shape of the defect, and the positions of transducer units and sensor units, according to an embodiment of the present invention. FIG. 18 is a graph showing relative amplitudes of reflected waves measured by sensor units in the experiment described with reference to FIG. 17. The transducer units and the sensor units are also disposed at an angle of 60 degrees.

In the configuration illustrated in FIG. 17, a wave frequency was 500 kHz, and it was generated by the array transducer. As a result, as illustrated in FIG. 18, the largest measurement value was detected by a sensor unit corresponding to an angle of a slit-shaped crack (240 degrees).

Figure 19:
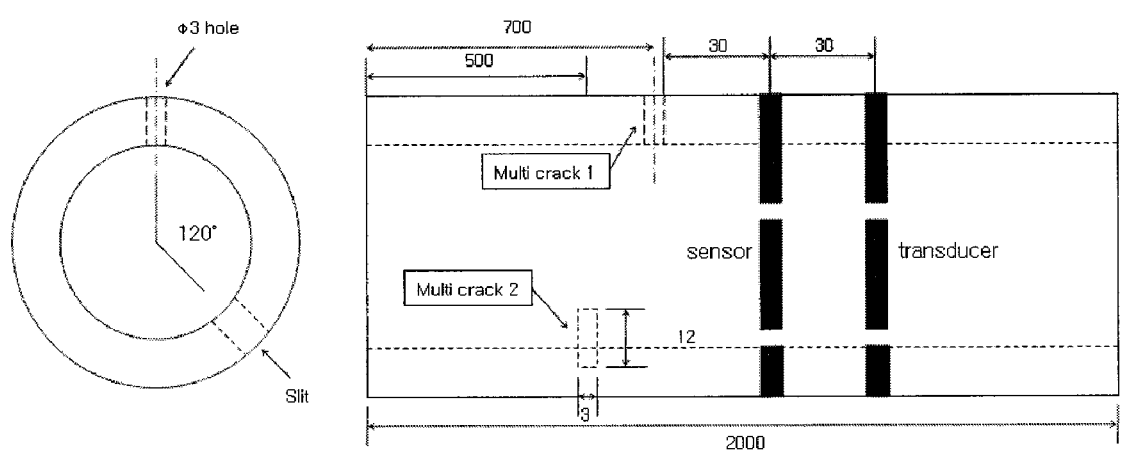
FIG. 19 is a schematic view illustrating a cross-section of a pipe used in another experiment for detecting the position of a defect, and the position and shape of the defect, and the positions of a transducer and a sensor, according to an embodiment of the present invention.
Figure 20:
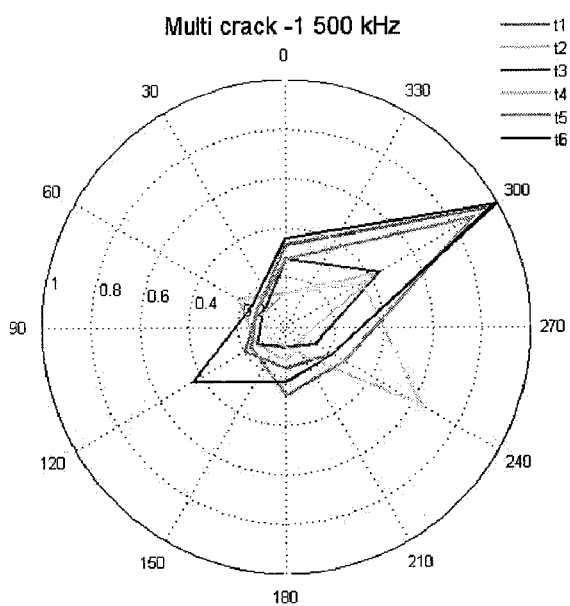
FIGS. 20 and 21 are graphs showing relative amplitudes of reflected waves measured in sensor units in the experiment described with reference to FIG. 19.
Figure 21:
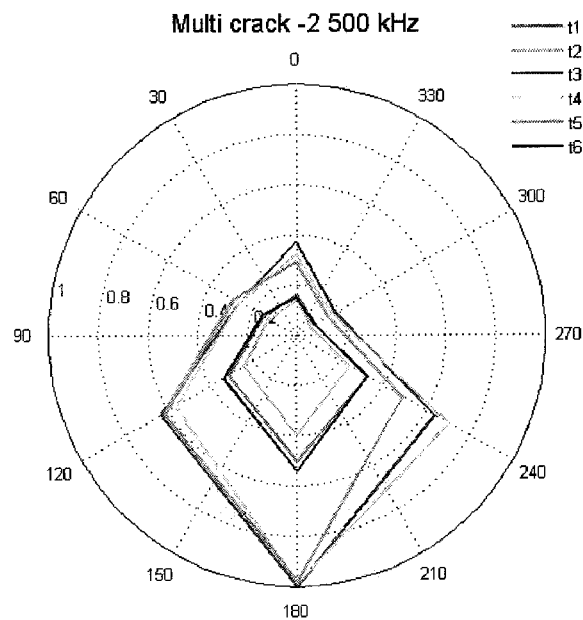

FIG. 19 is a schematic view illustrating a cross-section of a pipe used in another experiment for detecting a defect, and the position and shape of the defect, and the positions of transducer units and sensor units, according to an embodiment of the present invention. FIGS. 20 and 21 are graphs showing relative amplitudes of reflected waves measured by sensor units in the experiment described with reference to FIG. 19. The transducer units and the sensor units are also disposed at an angle of 60 degrees with respect to each other.

In the configuration illustrated in FIG. 19, a wave frequency was 500 kHz, and a vibration was applied using an array transducer and measured using an array sensor. As a result, as illustrated in FIGS. 20 and 21, the largest value was measured by sensor units corresponding to angles of cracks of 300 degrees and 180 degrees.

Hereinafter, a method of controlling the propagating direction of a shear wave generated by using an array transducer according to the present invention or focusing the shear wave toward a predetermined point will be described.

Figure 22:
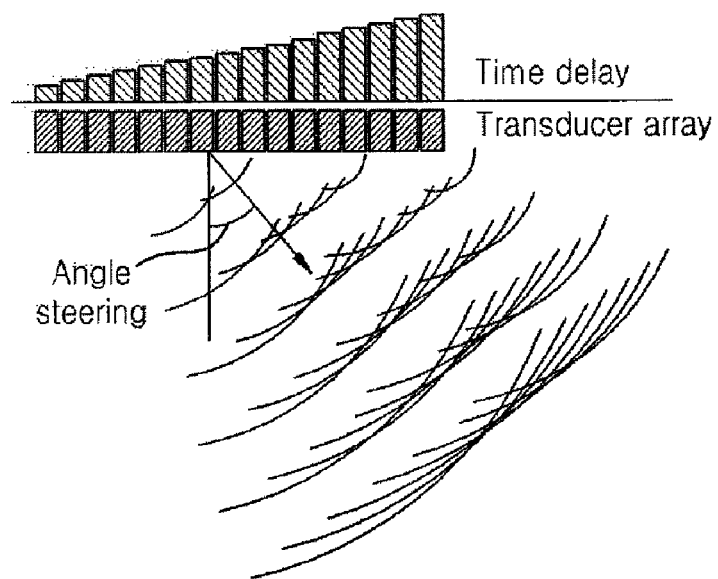
FIG. 22 illustrates a method of changing a propagating direction of a shear wave by using an array transducer according to an embodiment of the present invention.
Figure 23:
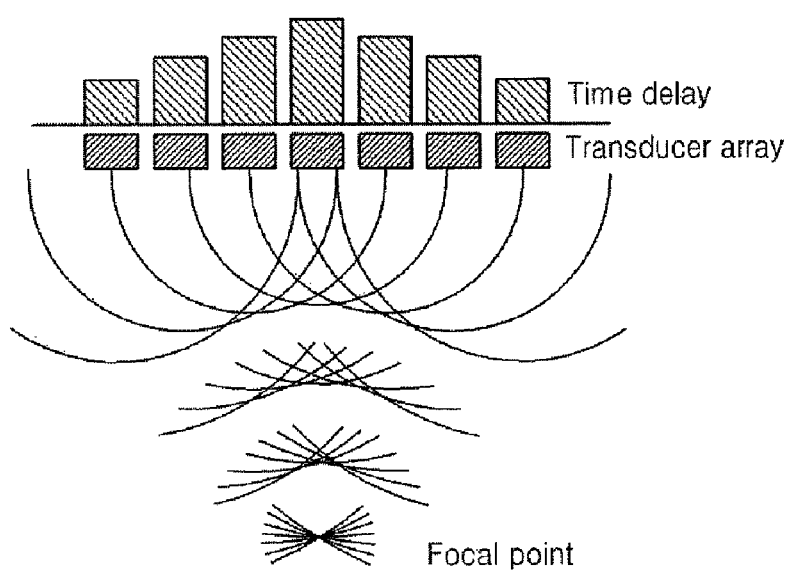
FIG. 23 is a schematic view illustrating a method in which a shear wave is focused toward a predetermined point by using an array transducer according to an embodiment of the present invention.
Figure 24:
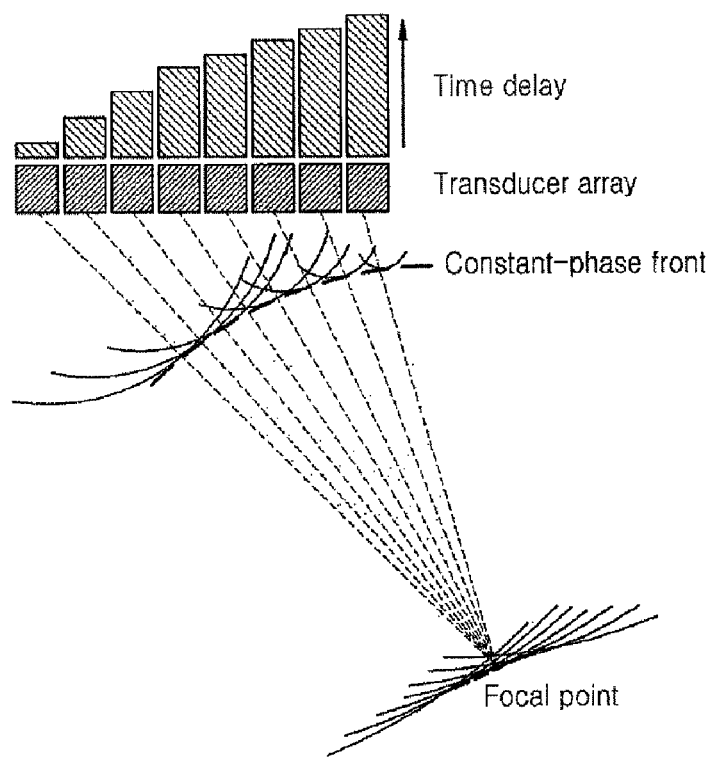
FIG. 24 is a schematic view illustrating a method of combining time delay methods illustrated in FIGS. 22 and 23.

FIG. 22 illustrates a method of changing a propagating direction of a shear wave by using an array transducer according to an embodiment of the present invention. FIG. 23 is a schematic view illustrating a method of focusing a shear wave toward a predetermined point by using an array transducer according to an embodiment of the present invention. FIG. 24 is a schematic view illustrating a method of combining time delay methods illustrated in FIGS. 22 and 23.

Referring to FIG. 22, a plurality of transducer units that are serially arranged generate shear waves at identical time intervals, the shear waves having substantially the same amplitude. Shear waves generated by a plurality of transducer units interfere with each other. In consequence, a line formed by connecting constructive interference points is at a predetermined angle to a line that is perpendicular to a line that is formed by connecting positions of the transducer units. That is to say, when the transducer units serially arranged are vibrated at identical time intervals such that differences between time delay values of adjacent transducer units are the same, a propagating direction of the shear waves may be changed.

Referring to FIG. 23, a plurality of transducer units which are arranged in a series and generate shear waves having substantially the same amplitude are vibrated with reducing time delay values with respect to a central transducer unit among the transducer units. In this case, the shear waves may be focused at predetermined points at the frontal central part of the transducer units due to a constructive interference.

FIG. 24 is a schematic view illustrating a method of combining the time delay methods illustrated in FIGS. 22 and 23. Referring to FIG. 24, a plurality of transducer units are vibrated with the difference of the time delay values between the adjacent transducer units decreasing. In this case, the shear waves may be focused at predetermined points in front of the transducer units array due to a constructive interference.

As shown in FIGS. 22 through 24, time delays of the transducer units may generate vibrations at set times in order to adjust a propagating direction of shear waves, and the shear waves may be thus focused towards predetermined points of the rod member 202. Accordingly, the structural health of a predetermined area of a structure may be examined.

The magnet 206 described may be a permanent magnet or an electromagnet. Also, the rod member 202 may be a beam, a hollow pipe, or any longitudinal member.

Figure 25:
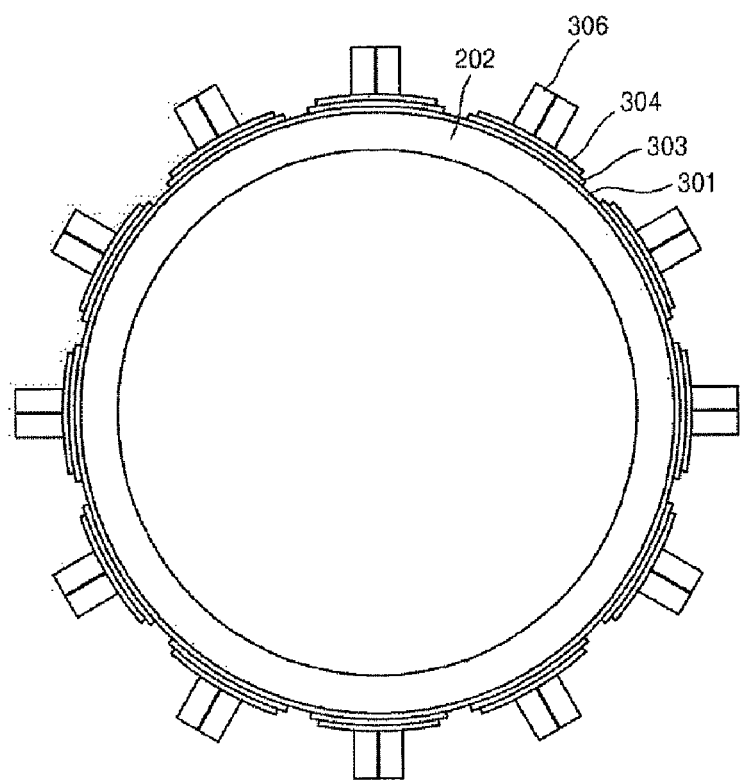
FIGS. 25 and 26 are cross-sectional views illustrating array transducers according to other embodiments of the present invention.
Figure 26:
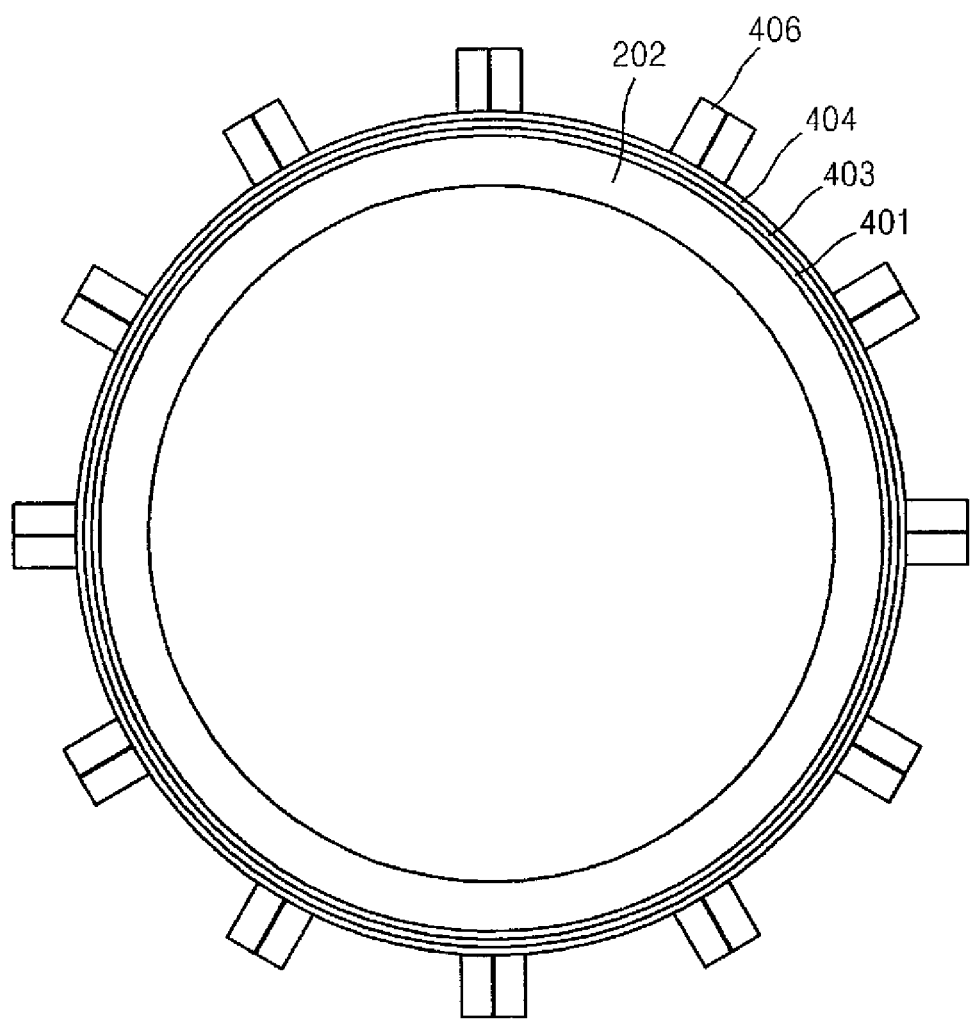

FIGS. 25 and 26 are cross-sectional views illustrating array transducers according to other embodiments of the present invention.

With regard to FIGS. 25 and 26, a magnetostrictive patch, an insulator, and a meander coil included in the array transducer are arranged in a segmented manner along a circumference of a rod member as illustrated in FIG. 8. However, in the embodiment described with reference to FIG. 25, the magnetostrictive patch is wound around a circumference of the rod member, and only the insulator and the meander coil are arranged in a segmented manner along the circumference of the rod member. Also, according to the embodiment described with reference to FIG. 25, a magnet is disposed above the meander coil. In other words, the magnetostrictive patch according to the present invention may be physically segmented or not be physically segmented, and the magnetostrictive patch may be divided into a plurality of portions, and magnetostriction may be generated in the divided portions.

Also, according to the embodiment described with reference to FIG. 26, the magnetostrictive patch, the insulator, and the meander coil are formed as a single unit wound around the rod member, and magnets are separated along the circumference of the rod member.

The magnets in the embodiments of FIG. 25 and FIG. 26 may be permanent magnets or electromagnets as described with reference to the previous embodiments. Also, the magnet may be installed along the circumference of the rod member or a position for applying a vibration may be selected and a magnet may be installed at this position. Also, the magnet may be installed at other position and a vibration may be applied at this position, thereby being possible to sequentially apply a vibration along the circumference of the rod member.

Meanwhile, if electromagnets are used, a plurality of electromagnets are installed along the circumference of the rod member, and a vibration may be applied or measured while varying a magnetic field which is sequentially formed by the electromagnets.

That is, according to the embodiments of FIGS. 25 and 26, the elements of the array transducer of the present invention may not be segmented as described with reference to FIGS. 6 through 9.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A segmented magnetostrictive patch array transducer comprising:
   a plurality of magnetostrictive patches attached along a circumference of a rod member;
   a plurality of insulators disposed on the magnetostrictive patches;
   a plurality of meander coils, each of the meander coils comprising a plurality of coil lines extending along the circumferential direction of the rod member on each of the insulators, wherein a current flows through adjacent coil lines in opposite directions to one another; and
   a magnetic field forming unit having a plurality of magnets that respectively form a magnetic field along the circumferential direction of the rod member on the magnetostrictive patches,
   wherein when a current is applied to at least one meander coil, the magnetostrictive patch located near the corresponding coil line of the meander coil is deformed due to magnetostriction so that a shear wave is generated along the rod member, or when the magnetostrictive patches are deformed due to a wave transmitted along the rod member, an electromotive force is generated in the meander coil due to an inverse magnetostrictive effect.

2. The segmented magnetostrictive patch array transducer of claim 1, wherein a distance between the coil lines is half of a wavelength of the generated shear wave.

3. The segmented magnetostrictive patch array transducer of claim 1, wherein the magnets are respectively disposed between the magnetostrictive patches.

4. A structural fault diagnosing apparatus comprising:
   a magnetostrictive patch that is attached to a surface of a rod member and is formed of a ferromagnetic material;
   an insulator that is disposed on the magnetostrictive patch;
   a meander coil that comprises a plurality of coil lines extending along a circumferential direction of the rod member on the insulator, wherein a current flows through adjacent coil lines in opposite directions to one another;
   at least one magnet that forms a magnetic field along the circumferential direction of the rod member on the magnetostrictive patch; and
   an array sensor comprising a plurality of sensor units, wherein when a current flows through the meander coil, the magnetostrictive patch deforms due to a magnetostrictive effect so that a shear wave is generated along the rod member, and the plurality of sensor units that are disposed at predetermined intervals along the circumferential direction of the rod member sense the shear wave.

5. The structural fault diagnosing apparatus of claim 4, wherein the array sensor comprises:
   a plurality of magnetostrictive patches attached to a circumference of the rod member;
   a plurality of insulators that are respectively disposed on the plurality of the magnetostrictive patches;
   a plurality of meander coils, each of the meander coils comprising a plurality of coil lines extending along a circumferential direction of the rod member on the insulators, wherein a current flows through adjacent coil lines in opposite directions to one another; and
   a magnetic field forming unit that forms a magnetic field along a circumferential direction of the rod member on the magnetostrictive patches,
   wherein an electromotive force is generated in the meander coil due to an inverse magnetostrictive effect as the magnetostrictive patches are deformed due to a shear wave, and an amplitude of the shear wave is measured by measuring the electromotive force.

6. The structural fault diagnosing apparatus of claim 4, wherein a distance between the coil lines is half of a wavelength of a generated shear wave.

7. A method of operating a segmented magnetostrictive patch array transducer, wherein the segmented magnetostrictive patch array transducer comprises:
   a plurality of magnetostrictive patches attached along a circumference of a rod member;
   a plurality of insulators that are respectively disposed on the magnetostrictive patches;
   a plurality of meander coils, each of the meander coils comprising a plurality of coil lines extending along a circumferential direction of the rod member on the insulators, wherein a current flows through adjacent coil lines in opposite directions to one another; and
   a magnetic field forming unit that forms a magnetic field along the circumferential direction of the rod member on the magnetostrictive patches,
   wherein when a current is applied to at least one meander coil, a magnetostrictive patch located near the corresponding coil line of the meander coil is deformed due to magnetostriction so that a shear wave is generated along the rod member, or when the magnetostrictive patch is deformed due to a wave transmitted along the rod member, an electromotive force is generated in the meander coil due to an inverse magnetostrictive effect,
   the method comprising:
   controlling instants of times when a current is applied to each of the meander coils in order to control instants of times when shear waves are generated using a deformation of each of the magnetostrictive patches so as to control points where waves respectively generated from each of the magnetostrictive patches and transmitted along the rod member generate a constructive interference.

8. A segmented magnetostrictive patch array transducer comprising:
   a magnetostrictive patch attached along a circumference of a rod member;
   an insulator that is disposed on the magnetostrictive patch;
   a plurality of meander coils, each of the meander coils comprising a plurality of coil lines extending along a circumferential direction of the rod member on the insulator, wherein a current flows through adjacent coil lines in opposite directions to one another; and
   a magnetic field forming unit that forms a magnetic field along the circumferential direction of the rod member on the magnetostrictive patch, wherein an area on the magnetostrictive patch wound around the circumference of the rod member is divided into a plurality of portions along the circumference of the rod member, and the plurality of meander coils are arranged to respectively correspond to the divided portions of the area, wherein when a current is applied to at least one of the meander coils, the magnetostrictive patch located near the corresponding meander coil is deformed due to magnetostriction so that a shear wave is generated along the rod member, or when the magnetostrictive patch is deformed due to a wave transmitted along the rod member, an electromotive force is generated in the meander coil due to an inverse magnetostrictive effect.

9. A segmented magnetostrictive patch array transducer comprising:
- a magnetostrictive patch attached along a circumference of a rod member;
- an insulator that is disposed on the magnetostrictive patch to cover the magnetostrictive patch;
- a meander coil that comprises a plurality of coil lines extending along a circumferential direction of the rod member on the insulator, wherein a current flows through adjacent coil lines in opposite directions to one another; and
- a magnetic field forming unit that forms a magnetic field along a circumferential direction of the rod member on the magnetostrictive patch, wherein when a current is applied to the meander coil, the magnetostrictive patch located near the corresponding meander coil is deformed due to magnetostriction so that a shear wave is generated along the rod member, or when the magnetostrictive patch is deformed due to a wave transmitted along the rod member, an electromotive force is generated in the meander coil due to an inverse magnetostrictive effect.

10. The segmented magnetostrictive patch array transducer of claim 9, wherein the magnetic field forming unit comprises a plurality of electromagnets that are separated apart from one another along the circumference of the rod member.

* * * * *